US00PP30504P2

(12) United States Plant Patent
Lang

(10) Patent No.: US PP30,504 P2
(45) Date of Patent: May 14, 2019

(54) ***KALANCHOE* PLANT NAMED 'DOKALMIKE'**

(50) Latin Name: *Kalanchoe blossfeldiana*
Varietal Denomination: Dokalmike

(71) Applicant: DUMMEN GROUP B.V., De Lier (NL)

(72) Inventor: Chunting Lang, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,279

(22) Filed: Feb. 16, 2018

(51) Int. Cl.
*A01H 5/02* (2018.01)

(52) U.S. Cl.
USPC ..... Plt./335

(58) Field of Classification Search
USPC ..... Plt./263.1, 335
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Kalanchoe* plant named 'Dokalmike', characterized by its compact, upright and uniformly mounded plant habit; moderately vigorous growth habit; freely branching plant habit; glossy dark green-colored leaves; uniform, early and freely flowering habit; large bright red purple-colored flowers; and excellent postproduction longevity.

2 Drawing Sheets

Botanical designation: *Kalanchoe blossfeldiana.*
Cultivar denomination: 'DOKALMIKE'.

BACKGROUND OF THE INVENTION

The present invention relates to a new and distinct *Kalanchoe* plant, botanically known as *Kalanchoe blossfeldiana* and hereinafter referred to by the name 'Dokalmike'.

The new *Kalanchoe* is a product of a planned breeding program conducted by the Inventor in De Lier, The Netherlands. The objective of the breeding program is to create new freely-branching and freely-flowering *Kalanchoe* plants with attractive leaf and flower coloration.

The new *Kalanchoe* plant originated from a cross-pollination made by the Inventor in De Lier, The Netherlands in 2012 of *Kalanchoe blossfeldiana* 'Sin-Li', not patented, as the female, or seed, parent with *Kalanchoe blossfeldiana* 'Fikalrudak', disclosed in U.S. Plant Pat. No. 27,913, as the male, or pollen, parent. The new *Kalanchoe* plant was discovered and selected by the Inventor as a single flowering plant from within the progeny of the stated cross-pollination in a controlled environment in De Lier, The Netherlands in April, 2013.

Asexual reproduction of the new *Kalanchoe* plant by vegetative terminal cuttings in a controlled environment in De Lier, The Netherlands since 2013 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Dokalmike'. These characteristics in combination distinguish 'Dokalmike' as a new and distinct *Kalanchoe* plant:

1. Compact, upright and uniformly mounded plant habit.
2. Moderately vigorous growth habit.
3. Freely branching plant habit.
4. Glossy dark green-colored leaves.
5. Uniform, early and freely flowering habit.
6. Large bright red purple-colored flowers.
7. Excellent postproduction longevity.

Plants of the new *Kalanchoe* can be compared to plants of the female parent, 'Sin-Li'. Plants of the new *Kalanchoe* differ from plants of 'Sin-Li' in the following characteristics:

1. Plants of the new *Kalanchoe* have smaller leaves than plants of 'Sin-Li'.
2. Plants of the new *Kalanchoe* flower later than plants of 'Sin-Li'.
3. Plants of the new *Kalanchoe* and 'Sin-Li' differ in flower color as flowers of plants of 'Sin-Li' are light pink and yellowish pink in color.

Plants of the new *Kalanchoe* can be compared to plants of the male parent, 'Fikalrudak'. Plants of the new *Kalanchoe* differ from plants of 'Fikalrudak' in the following characteristics:

1. Plants of the new *Kalanchoe* are not as compact as plants of 'Fikalrudak'.
2. Plants of the new *Kalanchoe* have smaller leaves than plants of 'Fikalrudak'.
3. Plants of the new *Kalanchoe* have larger flowers than plants of 'Fikalrudak'.
4. Plants of the new *Kalanchoe* and 'Fikalrudak' differ in flower color as flowers of plants of 'Fikalrudak' are darker red purple in color.

Plants of the new *Kalanchoe* can be compared to plants of the *Kalanchoe blossfeldiana* 'Kerinci', disclosed in U.S. Plant Pat. No. 10,031. In side-by-side comparisons, plants of the new *Kalanchoe* differ primarily from plants of 'Kerinci' in the following characteristics:

1. Plants of the new *Kalanchoe* are more compact than plants of 'Kerinci'.
2. Plants of the new *Kalanchoe* have smaller leaves than plants of 'Kerinci'.
3. Plants of the new *Kalanchoe* have larger flowers than plants of 'Kerinci'.
4. Plants of the new *Kalanchoe* and 'Kerinci' differ in flower color as flowers of plants of 'Kerinci' are duller red purple in color.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet is a side perspective view of a typical flowering plant of 'Dokalmike' grown in a container.

The photograph on the second sheet is a close-up view of a typical open flower and flower buds of 'Dokalmike'.

DETAILED BOTANICAL DESCRIPTION

The aforementioned photographs and following observations, measurements and values describe plants grown during the autumn in 10-cm containers in a glass-covered greenhouse in De Lier, The Netherlands and under cultural practices typical of commercial *Kalanchoe* production. During the production of the plants, day and night temperatures ranged from 20° C. to 21° C. and light levels ranged from 10,000 lux to 55,000 lux. Plants received long day/short night conditions (more than 14 hours of light) for four weeks then plants received photoinductive short day/long night conditions (minimum 14 hours darkness) until flowering. Plants were 14 weeks old when the photographs were taken and 13 weeks old when the description was taken. In the detailed description, color references are made to The Royal Horticultural Society Colour Chart, 2007 Edition, except where general terms of ordinary dictionary significance are used.

Botanical classification: *Kalanchoe blossfeldiana* 'Dokalmike'.

Parentage:

*Female, or seed, parent.*—*Kalanchoe blossfeldiana* 'Sin-Li', not patented.

*Male or pollen parent.*—*Kalanchoe blossfeldiana* 'Fikalrudak', disclosed in U.S. Plant Pat. No. 27,913.

Propagation:

*Type.*—By vegetative terminal cuttings.

*Time to initiate roots, summer.*—About eleven days at temperatures about 21° C.

*Time to initiate roots, winter.*—About two weeks at temperatures about 21° C.

*Time to produce a rooted young plant, summer.*—About 20 days at temperatures about 21° C.

*Time to produce a rooted young plant, winter.*—About four weeks at temperatures about 21° C.

*Root description.*—Fine, fibrous; typically greyish white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Compact, upright and uniformly mounded plant habit; freely flowering habit with numerous cymes positioned above the foliar plane; triangular in shape with rounded crown; appropriate for 10 to 15-cm containers; moderately vigorous growth habit.

*Plant height at flowering.*—About 19 cm.

*Plant diameter at flowering.*—About 20 cm.

*Branching habit.*—Freely branching habit with about seven to nine lateral branches developing per plant; pinching (removal of the terminal apex) is not required but will enhance lateral branch development.

Lateral branch description:

*Length.*—About 12 cm to 16 cm.

*Diameter.*—About 3 mm to 5 mm.

*Internode length.*—About 2 cm to 3 cm.

*Aspect.*—Mostly upright.

*Strength.*—Moderately strong.

*Texture.*—Smooth, glabrous.

*Color.*—Close to 146A.

Leaf description:

*Arrangement.*—Opposite, simple; generally symmetrical.

*Quantity per plant.*—Typically about 8 to 13 mature leaves and about 14 to 22 generative leaves.

*Length.*—About 10 cm.

*Width.*—About 7.5 cm.

*Shape.*—Ovate to elliptical.

*Apex.*—Acute to obtuse.

*Base.*—Obtuse.

*Margin.*—Vaulted.

*Texture and luster, upper and lower surfaces.*—Smooth, glabrous; coriaceous; succulent; glossy.

*Venation pattern.*—Pinnate.

*Color.*—Developing and fully developed leaves, upper surface: Close to 137A; venation, close to 137A. Developing and fully developed leaves, lower surface: Close to 137C; venation, close to 137C.

*Petioles.*—Length: About 1.5 cm. Diameter: About 4 mm to 8 mm. Texture, upper and lower surfaces: Smooth, glabrous; coriaceous; succulent. Color, upper surface: Close to 137A to 137B. Color, lower surface: Close to 137C.

Flower description:

*Flower arrangement and habit.*—Single flowers arranged in axillary cymes; uniform and freely flowering habit with usually more than 25 open flowers and more than 25 flower buds per lateral branch and more than 150 open flowers and flower buds developing per plant; plants flower continuously for at least seven weeks.

*Fragrance.*—None detected.

*Natural flowering season.*—Plants of the new *Kalanchoe* initiate and develop flowers under short day/long night conditions or during November and December in the Northern Hemisphere; flower initiation and development can also be induced under artificial short day/long conditions (at least 14 hours of darkness).

*Time to flower*.—Early flowering habit, under short day/long night photoinductive conditions, plants begin flowering about nine to eleven weeks; actual time to flower is primarily dependent upon temperature and light intensity.

*Post-production longevity*.—Excellent post-production longevity; plants maintain good foliage and flower substance for about 58 days under interior conditions; individual flowers last about 23 days on the plant; flowers persistent.

*Flower diameter*.—About 1.9 cm.

*Flower length* (*height*).—About 1.3 cm.

*Flower buds*.—Shape: Initially oblong, becoming tubular ovoid with development. Color, before flower opening: Close to 62D and 58D.

*Petals*.—Arrangement: Four in a single whorl. Length: About 9 mm. Width: About 7.5 mm. Aspect: Flat. Shape: Rounded. Apex: Acute. Base: Obtuse. Margin: Entire. Texture and luster, upper and lower surfaces: Smooth, glabrous; shiny. Color: When opening and fully opened, upper surface: Close to 67C; color does not change with development. When opening and fully opened, lower surface: Close to between 58D and 67D; color does not change with development.

*Sepals*.—Appearance: Four in a single whorl. Length: About 9 mm. Width: About 2.5 mm. Shape: Oblong, pointed. Apex: Acute. Base: Rounded. Margin: Entire. Aspect: Upright, rigid. Texture and luster, upper and lower surfaces: Smooth; glabrous; shiny. Color, upper and lower surfaces: Close to 139D.

*Peduncles*.—Length: About 3 mm to 4 mm. Diameter: About 1 mm to 2 mm. Aspect: Erect, rigid. Strength: Moderately strong. Texture: Smooth, glabrous. Color: Close to 139D.

*Reproductive organs*.—Androecium: Stamen number: About eight per flower. Anther shape: Elliptic, flat. Anther length: About 0.3 mm. Anther color: Close to 150D. Amount of pollen: Scarce. Pollen color: Close to 12A. Gynoecium: Pistil number: About four. Pistil length: About 1 cm. Style length: About 7 mm. Style color: Close to 138D. Stigma shape: Flat. Stigma color: Close to 8D. Ovary color: Close to 138D.

*Seeds*.—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen & pest resistance: Plants of the new *Kalanchoe* have not been observed to be resistant to pests and pathogens common to *Kalanchoe* plants to date.

It is claimed:

1. A new and distinct *Kalanchoe* plant named 'Dokalmike' as illustrated and described.

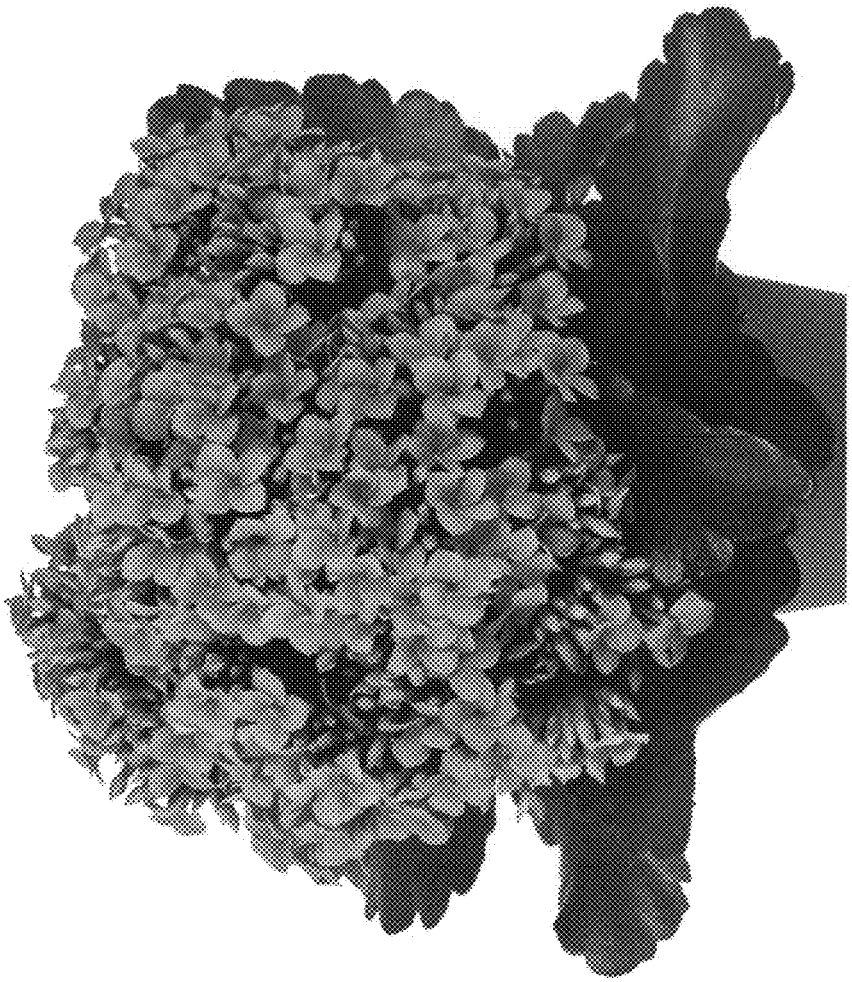

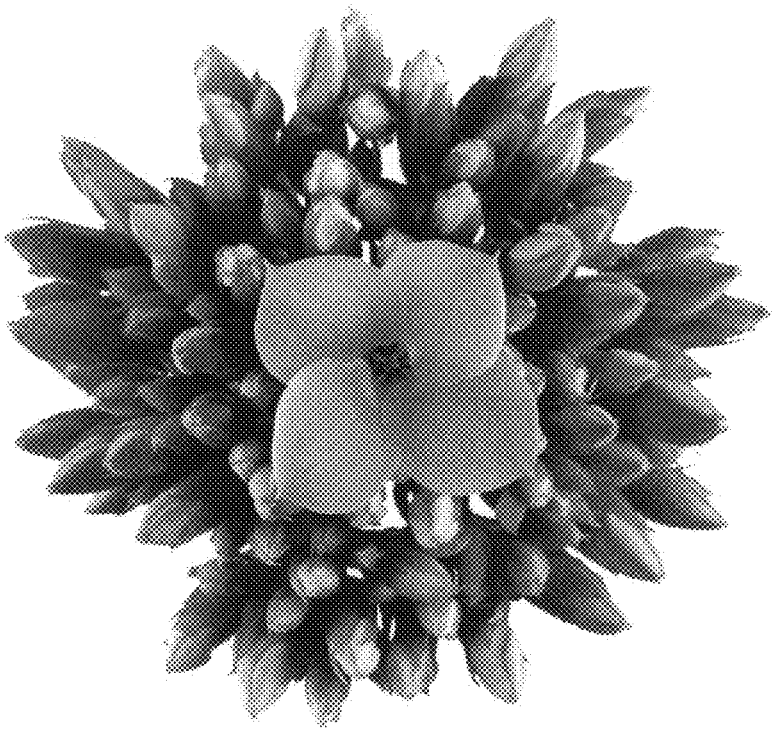

* * * * *